United States Patent [19]
Dempf et al.

[11] 4,152,359
[45] May 1, 1979

[54] STABILIZED 1,1,1-TRICHLOROETHANE

[75] Inventors: Dominik Dempf, Mehring-Öd;
Rudolf Knabl, Burghausen, both of
Fed. Rep. of Germany

[73] Assignee: Wacker-Chemie GmbH, Munich,
Fed. Rep. of Germany

[21] Appl. No.: 880,752

[22] Filed: Feb. 24, 1978

[30] Foreign Application Priority Data

Apr. 19, 1977 [DE] Fed. Rep. of Germany ....... 2717322

[51] Int. Cl.$^2$ ............................................ C07C 17/40
[52] U.S. Cl. ............................................ 260/652.5 R
[58] Field of Search ................................ 260/652.5 R

[56] References Cited
U.S. PATENT DOCUMENTS

| 3,564,063 | 2/1971 | Cormany et al. | 260/652.5 R |
| 3,878,256 | 4/1975 | Richtzenhain et al. | 260/652.5 R |
| 3,935,287 | 1/1976 | Beckers et al. | 260/652.5 R |

Primary Examiner—C. Davis
Attorney, Agent, or Firm—Hammond & Littell

[57] ABSTRACT

A stabilized 1,1,1-trichloroethane containing, as stabilizer, from
0.1% to 1% by weight of 2,3-epoxy-1-propanol,
1% to 3% by weight of 1,4-dioxane, and
0.1% to 0.5% by weight of butylene 1,2-oxide.

2 Claims, No Drawings

STABILIZED 1,1,1-TRICHLOROETHANE

BACKGROUND OF THE INVENTION 1,1,1-trichloroethane is used inter alia as a solvent for cleaning and removing grease from metal articles or for chemical cleaning. For these purposes, chemical stabilization to prevent decomposition is an absolute necessity. Stabilizing agents for chlorinated hydrocarbons, such as 1,1,1-trichloroethane, are known and are in common use. The stabilizer must, however, be chosen specifically for the respective chlorinated hydrocarbon. It is impossible to make predictions in respect of the stabilizing properties of certain classes of chemical substances; knowledge of stabilizing property of a compound for one chlorinated hydrocarbon cannot be assumed to be applicable to other chlorinated hydrocarbons.

A wide variety of compounds or mixtures are generally used to stabilize 1,1,1-trichloroethane. The most important compound is nitromethane, but epoxides, alcohols, ethers, olefins, amines, alkoxyalkanes, ketones, nitriles and organic esters are also, or have been, used. Usually mixtures of the said substances are used. The disadvantage of hitherto known stabilizer mixtures is that large quantities of the stabilizers must be added to the 1,1,1-trichloroethane to be stabilized in order to achieve effective stabilization. This results in changes in the properties of the stabilized 1,1,1-trichloroethane.

OBJECTS OF THE INVENTION

An object of the present invention is to find a stabilizer mixture for 1,1,1-trichloroethane, the individual constituents of which have a synergistic influence on stabilization.

Another object of this invention is the development of a stabilized 1,1,1-trichloroethane containing, as stabilizer, from
0.1% to 1% by weight of 2,3-epoxy-1-propanol,
1% to 3% by weight of 1,4-dioxane, and
0.1% to 0.5% by weight of butylene 1,2-oxide.

These and other objects of the invention will become more apparent as the description thereof proceeds.

DESCRIPTION OF THE INVENTION

The subject of the invention is stabilized 1,1,1-trichloroethane, which is characterized in that it contains from
0.1% to 1% by weight of 2,3-epoxy-1-propanol,
1% to 3% by weight of 1,4-dioxane, and
0.1% to 0.5% by weight of butylene 1,2-oxide.

More particularly, the present invention relates to a stabilized 1,1,1-trichloroethane containing, as stabilizer, from
0.1% to 1% by weight of 2,3-epoxy-1-propanol,
1% to 3% by weight of 1,4-dioxane, and
0.1% to 0.5% by weight of butylene 1,2-oxide.

Optionally, in addition to the above synergistic stabilizer mixture, one or several of the following compounds can be used in addition: 1,3-dioxane, 1,3,5-trioxane, epichlorohydrin, cyclohexene oxide, a nitroalkane having 1 to 3 carbon atoms. These compounds can be employed in amounts of from 0 to 1% by weight.

The individual components of the stabilizer mixture have already been used as additives in other stabilizer mixtures, but the advantageous effect of this stabilizer combination had not previously been realized. None of the compounds, 2,3-epoxypropanol, 1,4-dioxane and butylene 1,2-oxide have the desired effect when used individually. Combinations of, for example, 1,4-dioxane and butylene 1,2-oxide are also significantly less effective by comparison with the combination according to the invention. If 2,3-epoxy-1-propanol is replaced by derivatives such as, for example, phenyl glycidyl ether or methyl glycidyl ether, no synergism is observed.

The stability of a mixture of 1,1,1-trichloroethane and the added compounds is tested by heating 300 ml of the respective mixture to boiling point with a 150 watt light bulb, in a 500 ml Erlenmayer flask fitted with a reflux condenser. Simultaneously, a stream of steam-saturated oxygen is passed into the solvent through a glass tube at a rate of 2 cc per minute. An aluminum strip (2×6 cm, Al 99.5%, Fe 0.3%) is so arranged that it is half-immersed in the liquid phase. A similar aluminum strip is disposed in the liquid at the bottom of the vessel. As a measure of the stabilizing effect, the time taken for a 0.02% by weight concentration of hydrogen chloride in the sample to be exceeded is determined. At the same time the aluminum strips are tested for corrosion. At a hydrogen chloride concentration of 0.02% by weight, it is not possible to discern any corrosion or discoloration of the sample. In addition, the aluminum strips have no patches of corrosion at this stage.

The stabilizing effect of the stabilizer combination mentioned increases in accordance with the concentration in the solvent. Only when the quantities added are in the upper range claimed is there no longer an increase in the stabilizing effect proportional to the quantity of stabilizer. Stabilized 1,1,1-trichloroethane mixtures are manufactured by adding the corresponding amount of chemicals to 1,1,1-trichloroethane, so that 100% results in each case.

The following examples are illustrative of the practice of the invention without being limitative in any manner.

EXAMPLE 1

500 ml of stabilized 1,1,1-trichloroethane containing 0.5% by weight of 2,3-epoxy-1-propanol, 3% by weight of 1,4-dioxane and 0.5% by weight of butylene 1,2-oxide were refluxed under the specified test conditions. The acidity limit of 0.02% by weight of hydrogen chloride was reached only after 1486 hours. After this period of time no indication of corrosion (pitting, discoloration) was observed on the aluminum strips either in the gas phase or in the liquid.

EXAMPLE 2

Stabilized 1,1,1-trichloroethane containing 1% by weight of 2,3-epoxy-1-propanol and otherwise the same stabilizer contents as in Example 1 was tested according to the test conditions. The hydrogen chloride concentration limit of 0.02% by weight was reached only after 1890 hours. No corrosion could be detected on the aluminum strips.

EXAMPLE 3 (Comparison Example)

1,1,1-trichloroethane containing 0.5% by weight of 2,3-epoxy-1-propanol and no other stabilizers achieved a test time of merely 353 hours under the test conditions mentioned. Corrosion in the form of pitting appeared on the aluminum strips.

EXAMPLE 4 (Comparison Example)

1,1,1-trichloroethane containing 3% by weight of 1,4-dioxane and 0.5% by weight of butylene 1,2-oxide achieved a test time of 621 hours.

EXAMPLE 5

The above-mentioned stabilizer values and further combinations are compiled in Table 1. This summary clearly shows the synergistic effect of the claimed stabilizer combinations.

Table 1

The effect of different stabilizers on the stability of 1,1,1-trichloroethane in the presence of aluminum.

| Example | Stabilizer | Concentrations % by weight | Time taken for 0.02% by weight of HCl to be reached in hours | State of the aluminum strips after test |
|---|---|---|---|---|
| 3 | EPOP(*) | 0.5 | 353 | pitting |
|  | EPOP | 0.5 |  |  |
| 1 | 1,4-dioxane | 3.0 | 1486 | no corrosion |
|  | butylene 1,2-oxide | 0.5 |  |  |
|  | EPOP | 1 |  |  |
| 2 | 1,4-dioxane | 3.0 | 1890 | no corrosion |
|  | butylene 1,2-oxide | 0.5 |  |  |
|  | EPOP | 0.05 |  |  |
|  | 1,4-dioxane | 3 | 115 | no corrosion |
|  | butylene 1,2-oxide | 0.5 |  |  |
|  | EPOP | 0.5 |  |  |
|  | 1,3,5-trioxane | 0.5 | 1399 | no corrosion |
|  | methyl-EPOP(**) | 0.5 |  |  |
|  | 1,4-dioxane | 3.0 | 160 | grey coating in the gas phase |
|  | butylene 1,2-oxide | 0.5 |  |  |
|  | dimethoxyethane | 0.5 |  |  |
|  | EPOP | 0.5 | 400 | corrosion in the gas phase |
|  | 1,4-dioxane | 3.0 |  |  |
|  | butylene 1,2-oxide | 0.5 |  |  |
|  | phenyl-EPOP(*) | 0.5 |  |  |
|  | dioxane | 3.0 | 130 | grey coating in gas phase |
|  | butylene 1,2-oxide | 0.5 |  |  |
| 4 | 1,4-dioxane | 3.0 |  |  |
|  | butylene 1,2-oxide | 0.5 | 621 | corrosion in gas phase |
|  | butylene 1,2-oxide | 0.5 | 30 | corrosion in gas phase and liquid phase |
|  | 1,4-dioxane | 3.0 |  |  |
|  | butylene 1,2-oxide | 0.5 | 600 | corrosion in liquid phase |
|  | nitromethane | 0.5 |  |  |
|  | 1,4-dioxane | 3.0 |  |  |
|  | butylene 1,2-oxide | 0.5 | 1400 | no corrosion |
|  | EPOP | 0.5 |  |  |
|  | nitromethane | 0.5 |  |  |

(*) 2,3-epoxy-1-propanol (glycidol)
(**) methyl ester of glycidol
(*) phenyl ether of glycidol The preceding specific embodiments are illustrative of the practice of the invention. It is to be understood, however, that other expedients known to those skilled in the art, or disclosed herein, may be employed without departing from the spirit of the invention or the scope of the appended claims.

We claim:
1. A stabilized 1,1,1-trichloroethane containing, as stabilizer, from
0.1% to 1% by weight of 2,3-epoxy-1-propanol,
1% to 3% by weight of 1,4-dioxane, and
0.1% to 0.5% by weight of butylene 1,2-oxide.
2. The stabilized 1,1,1-trichloroethane of claim 1 having a further content of up to 1% by weight of a stabilizer selected from the group consisting of 1,3-dioxane, 1,3,5-trioxane, epichlorohydrin, cyclohexene oxide, a nitroalkane having from 1 to 3 carbon atoms and mixtures thereof.

* * * * *